United States Patent [19]

Urakami et al.

[11] 4,033,821
[45] July 5, 1977

[54] PROCESS FOR PRODUCING YEAST CELLS

[75] Inventors: Teizi Urakami; Reiko Michimi, both of Niigata, Japan

[73] Assignee: Mitsubishi Gas Chemical Company, Inc., Tokyo, Japan

[22] Filed: Apr. 9, 1976

[21] Appl. No.: 675,551

Related U.S. Application Data

[63] Continuation-in-part of Ser. No. 539,603, Jan. 8, 1975, abandoned.

[30] Foreign Application Priority Data

Jan. 14, 1974 Japan .............................. 49-7387

[52] U.S. Cl. .................................. 195/49; 195/82
[51] Int. Cl.$^2$ .................... C12C 11/08; C12B 1/00
[58] Field of Search ............................ 195/49, 82

[56] References Cited

UNITED STATES PATENTS 3,929,578  12/1975  Urakami et al. ..................... 195/49

FOREIGN PATENTS OR APPLICATIONS 7,224,754  7/1972  Japan ................................... 195/49

OTHER PUBLICATIONS

Ishizaka, et al., "Yeast Production from Methanol," Chemical Abstracts, vol. 77, No. 5, p. 378, abs. no. 32739d, (1972).

Primary Examiner—Alvin E. Tanenholtz
Assistant Examiner—Thomas G. Wiseman
Attorney, Agent, or Firm—Birch, Stewart, Kolasch and Birch

[57] ABSTRACT

A process for producing yeast cells by culturing in a culture liquor containing methanol and/or ethanol as main carbon sources a yeast belonging to the species *Pichia aganobii* and capable of assimilating methanol and/or ethanol, and separating the cells of said yeast from the culture liquor.

6 Claims, No Drawings
}

PROCESS FOR PRODUCING YEAST CELLS

This application is a continuation-in-part of our prior U.S. application Ser. No. 539,603, filed Jan. 8, 1975, now abandoned.

This invention relates to a process for producing yeast cells by use of a novel yeast. More particularly, the invention pertains to a process for producing yeast cells by culturing in a culture liquor containing methanol and/or ethanol as main carbon sources a novel yeast belonging to Pichia, and separating the cells of said yeast from the culture liquor.

Heretofore, waste molasses, sulfite pulp waste liquors and n-paraffins have been used as carbon sources in culture media for the production of yeast cells. Recently, however, there are many literature references concerning processes for producing yeast cells by culturing yeasts with inexpensive carbon sources. In recent years, methanol and ethanol have come to the produced in large quantities with the progress of organic synthetic chemical industries, so that the said alcohols have come to be obtainable at low costs. These alcohols are water-soluble, and hence are suitable as carbon sources for use in yeast-culturing media and are most preferable as materials for fermentation of yeasts.

The present invention provides a process for producing yeast cells by culturing a novel yeast capable of assimilating methanol and/or ethanol as main carbon sources.

A few strains have been isolated from the soils of paddy fields at Kashiwazaki, Niigata; Miyagi; Nakanoguchigawa, Niigata; and Kamo, Niigata, all in Japan. They are considered to belong to the genus Pichia, but are different in various points from known yeasts belonging to said genus, as hereinafter described, so that the inventors have concluded that they are of new species and have named the species *Pichia aganobii*. Examples of the strains are designated as *Pichia aganobii* Y-16, Y-145, Y-410 and Y-1023, respectively, and they were deposited at the Fermentation Research Institute, Agency of Industrial Science and Technology, Chiba, Japan, and have been assigned reference numbers of FERM-P No. 2427, FERM-P No. 2428, FERM-P No. 2429 and FERM-P No. 2430, respectively, dated December 25th, 1973. The above strains were also deposited at Northern Utilization Research and Development Division, U.S. Department of Agriculture, Peoria, Illinois, U.S.A., and have been assigned NRRL Y-8159, Y-8160, Y-8161 and Y-8162, respectively, dated Mar. 29, 1976.

The microbiological properties of the above mentioned strains are as set forth below.

Microbiological properties of *Pichia aganobii* Y-16:

a. Growth state on various media:
 1. MY liquid medium, cultured at 28° C. for 2 to 7 days:
  Vegetative cells, 2 to 5 by 2 to 5 microns in size. Round, oval to short-ellipsoidal in shape, occurring singly or in pairs. No formation of pellicle. No formation of arthrospores. Reproduced by multilateral budding.
 2. MY agar medium, cultured at 28° C. for 4 days:
  i. Degree of growth: Abundant growth
  ii. Shape of circumference of colonies: Entire circumference
  iii. Raised state of colonies: Pulvinate or convex
  iv. Shape of surface of colonies: Smooth
  v. Gloss of colonies: Glistening
  vi. Nature of colonies: Butyrous
  vii. Color tone: Yellowish white
 3. Methanol-containing agar medium, (* note No. 2) cultured at 28° C. for 7 days:
  i. Degree of growth: Abundant growth
  ii. Shape of circumference of colonies: Entire circumference
  iii. Raised state of colonies: Convex or pulvinate
  iv. Shape of surface of colonies: Smooth
  v. Gloss of colonies: Glistening
  vi. Nature of colonies: Butyrous
  vii. Color tone: Yellowish white
 4. Giant colonies on MY agar medium, cultured at 20° C. for 20 days:
  i. Degree of growth: Abundant growth
  ii. Shape of circumference of colonies: Entire circumference
  iii. Raised state of colonies: Raised
  iv. Shape of surface of colonies: Smooth
  v. Gloss of colonies: Crctaceous
  vi. Nature of colonies: Butyrous
  vii. Color tone: White
 5. Slide culture on corn extract agar medium, cultured at 28° C. for 4 weeks:
  No formation of true mycelium nor pseudomycelium.
b. Formation of ascospores:
 Formation of ascospores was observed on malt agar medium and sodium acetate agar medium. The ascospores were hat-shaped and 1 to 4 in number.
c. Formation of ballistospores:
 No formation of ballistospores was observed on MY agar plate culture.
d. Physiological properties:
 1. Optimum growth conditions:
  Good growth at 20° to 35° C. Good growth was observed at pH 2 to 7.5.
 2. Growth ranges:
  Growth became bad at above 35° C. Growth became bad at above pH 7.5.
 3. Assimilation of nitrates: Negative
 4. Assimilation of arbutin: Positive
 5. Liquefaction of gelatin: Negative
 6. Formation of carotinoid pigment: Negative
 7. Formation of starch-like compounds: Negative
 8. Vitamin-requiring property: Biotin was absolutely required, and thiamine was stimulatively required.
 9. Coagulation of milk: Negative
 10. Osmotolerance: Salt tolerance, growth observed in an aqueous solution containing not more than 8 wt.% of sodium chloride.
 11. Assimilation of methanol or ethanol (* Note No. 3):
  Excellent growth with assimilation of methanol as carbon source even in the absence of other carbon sources. Good growth with assimilation of ethanol, although slowly.
 12. Urease test: Positive (weak)
 13. Splitting of fat: Negative
 14. Production of excess acid: Negative
 15. Formation of ester: Negative
e. Fermentation of saccharides:

| | |
|---|---|
| D-Glucose | + |
| D-Galactose | − |

-continued

| | |
|---|---|
| Sucrose | − |
| Maltose | − |
| Cellobiose | − |
| Trehalose | − |
| Lactose | − |
| Inulin | − |
| Raffinose | − |
| Melibiose | − |
| α-Methyl-D-glucoside | − |
| Soluble starch | − | f. Assimilation of various carbon sources:

| Carbon source | Assimilation |
|---|---|
| D-Arabinose | + (Slow) |
| L-Arabinose | ++ |
| D-Ribose | ++ |
| D-Xylose | ++ |
| D-Glucose | ++ |
| D-Mannose | ++ |
| D-Galactose | ++ |
| L-Rhamnose | − |
| Maltose | − |
| Sucrose | − |
| Lactose | − |
| Melibiose | − |
| Cellobiose | ++ |
| Trehalose | ++ |
| Raffinose | − |
| Melezitose | − |
| α-Methyl-D-glucoside | − |
| Soluble starch | − |
| Inulin | − |
| Erythritol | ++ |
| Inositol | − |
| D-Mannitol | ++ |
| Glycerin | ++ |
| DL-Lactic acid | − |
| Salicin | ++ |
| Succinic acid | ++ |
| Citric acid | + (Slow) |
| L-Sorbose | ++ |
| Arbutin | ++ |
| D-Glycitol | ++ |

Microbiological properties of *Pichia aganobii* Y-410:
Only the property different from those of *Pichia aganobii* Y-16 is set forth below.
f. Assimilation of various carbon sources:

| | |
|---|---|
| Citric acid | − |

Microbiological properties of *Pichia aganobii* Y-145:
Only the property different from those of *Pichia aganobii* Y-16 is set forth below.
f. Assimilation of various carbon sources:

| | |
|---|---|
| DL-Lactic acid | + (Slow) |
| Citric acid | − |

Microbiological properties of *Pichia aganobii* Y-1023:
Only the properties different from those of *Pichia aganobii* Y-16 are set forth below.
f. Assimilation of various sources:

| | |
|---|---|
| Citric acid | − |
| D-Arabinose | − |

Notes:
1. Tests are conducted according to Lodder's "The Yeasts, A Taxonomic Study", 1970 and Hiroshi Iizuka and Shoji Goto: "Method for Classification and Identification of Yeasts" (1969).
2. The methanol (or ethanol)-containing agar slant medium is prepared in the following manner:

In one liter of distilled water are dissolved 4 g. of $KH_2PO_4$, 3 g. of $(NH_4)_2SO_4$, 0.4 g. of $MgSO_4 \cdot 7H_2O$, 0.2 mg. of $FeSO_4 \cdot 7H_2O$, 5 mg. of $CaCl_2 \cdot 2H_2O$, 0.5 mg. of $MnSO_4 \cdot 4H_2O$, 0.5 mg. of $ZnSO_4 \cdot 7H_2O$, 4 μg. of biotin, 200 μg. of thiamine hydrochloride and 20 g. of agar. The resulting solution is adjusted to pH 4.7, sterilized for 20 minutes under 1 $kg/cm^2$ (gauge), and then aseptically incorporated with 10 g. of methanol (or ethanol).

3. The same liquid medium as Note 2 above is used, except that the agar is excluded.

In view of the fact that the above strains all form hat-shaped ascospore and no arthrospores nor ballistospores, and the cells are round or oval, reproduced by multilateral budding, form no pseudomycelium, do not assimilate nitrates and form no pellicle, as mentioned above, they are considered, according to Lodder: "The Yeasts, A Taxonomic Study" (1970), that they belong to the genus Pichia.

When the properties of the present yeasts are compared with those of the known strains described in the Lodder's work, the yeasts are similar to strains belonging to the species *Pichia farinosa* in that they assimilate galactose, and do not assimilate sucrose, maltose nor lactose, and ferment D-glucose, but differ therefrom in the various points, i.e. shape or surface of colonies, size of cells, formation of pellicle, formation of arthrospores, shape of ascospore, fermentation of galactose and trehalose, assimilation of D-arabinose, L-arabinose, L-sorbose, cellobiose, trehalose, lactose, D-xylose, ethanol, salicin, succinic acid, citric acid and methanol, splitting of arbutin, vitamin requiring property, and growth at 37° C. The present yeasts are the same as strains of *Pichia pinus* in the points, i.e., splitting arbutin and assimilating cellobiose and erythritol but neither sucrose, maltose nor lactose, but differ therefrom in fermentation of D-glucose, assimilation of D-arabinose, L-arabinose, D-mannose, D-galactose, L-rhammose, ethanol, citric acid and L-sorbose are urease test.

As is clear from the above-mentioned differences, the present yeasts do not coincide with the known yeasts described in the Lodder's work. Further, in view of the methanol and/or ethanol assimilation of the present yeasts, no yeasts coinciding with the present yeasts were found in the known strains. Accordingly, the present inventors concluded that the present yeasts belonged to a new species which is named *Pichia aganobii*.

The culture liquor used for cultivation of the present yeast may be any of a synthetic or natural medium so far as it contains methanol and/or ethanol as a main carbon source, and may further contain, proper amounts of nitrogen sources, inorganics, vitamins and other growth-promoting substances.

As the nitrogen sources, there are used nitrogen-containing substances such as ammonium salts, urea, corn steep liquor, casein, yeast extract and meat extract. In addition, it is also preferable to add inorganic salts such as calcium salts, magnesium salts, potassium salts, phosphates, manganese salts, zinc salts, iron salts and copper salts, and substances necessary for growth or growth-promoting substances such as vitamins and amino acids.

The culture liquor may contain 6 wt.% or less, preferably 3 wt.% or less, of methanol and/or ethanol. The propagation induction period of the present yeast is shorter and the evaporation loss of the methanol and/or ethanol from the culture liquor is less, as the initial concentration of the alcohol concentration in the culture liquor is lower, preferably 0.5 wt.% or less. The propagation induction period is longer, as the methanol and/or ethanol concentration is larger, when the alcohols are the only source for carbon. The period can also be controlled by further incorporating, up to 10 wt.%, other assimilable carbohydrates such as glucose into the culture liquor, in addition to the alcohol. In view of the above, it is better to control the alcohol concentration in the culture liquor as low as possible at the beginning of culturing and to keep the alcohol concentration at a constant level by only supplementing as much alcohol as that consumed. Furthermore, cultivation is conducted under aerobic conditions at a temperature of preferably 10° to 37° C., practically 20° to 33° C., more preferably 27° to 32° C., and at a pH of 7.5 or less, preferably 2 to 7. The type of cultivation may be any of the batch-wise or continuous culture procedures. In case an ammonium salt is used as the nitrogen source, ammonia is consumed during the cultivation owing to the formation of cells to lower the pH of the culture liquor. In order to maintain the pH of the culture liquor at a constant level during the cultivation, therefore, the pH of the culture liquor should be controlled by the addition of ammonia, potassium hydroxide or sodium hydroxide from time to time. Among these, ammonia is most preferred.

After completion of the cultivation carried out in the above-mentioned manner, the resulting cells are separated from the culture liquor by filtration or centrifugation. If necessary, the cells are washed.

The wet cells thus obtained are dried, and then may be utilized as feeds either as they are or after various treatments. Alternatively, from the thus obtained cells, endo-cellular substances such as nucleic acids, vitamins, coenzymes, proteins and lipids are extracted as pure substances or mixtures thereof, and these may be used as feeds, foods, medicines and industrial materials.

The present invention is illustrated in more detail below with reference to certain examples.

EXAMPLE 1

In one liter of pure water were dissolved 4 g. of $KH_2PO_4$, 3 g. of $(NH_4)_2SO_4$, 0.4 g. of $MgSO_4 \cdot 7H_2O$, 0.2 mg. of $FeSO_4 \cdot 7H_2O$, 5 mg. of $CaCl_2 \cdot 2H_2O$, 0.5 mg. of $MnSO_4 \cdot 4H_2O$, 0.2 mg. of $CuSO_4 \cdot 5H_2O$, 20 µg. of biotin and 1 mg. of thiamine hydrochloride, and the resulting solution was adjusted to pH 4.5 to prepare a culture liquor. 500 Milliliters of the culture liquor was charged into a 1-liter mino-jar and sterilized for 20 minutes under 1 kg/cm² (gauge), and then 5 g. of methanol was added thereto. Into this culture liquor was inoculated 2% by volume of a preculture liquor containing the cells of a yeast *Pichia aganobii* Y-16 which had been prepared by preculturing the yeast at 28° C. for 48 hours in a methanol-containing medium of the same composition as above at an initial pH of 5, and an aerobic stirring culture was conducted at 32° C. for 53 hours while adding ammonia water so as to maintain the culture liquor at pH 4.5. After completion of the cultivation, the culture liquor was centrifuged to collect wet cells, which were then dried at 80° C. for 24 hours to obtain dry cells in a proportion of 3.4 g. per liter of the culture liquor.

EXAMPLE 2

Example 1 was repeated, except that *Pichia aganobii* Y-410 was used in place of *Pichia aganobii* Y-16, and that the aerobic stirring culture was conducted at 28° C for 46 hours in place of 32° C for 53 hours. There was obtained 3.5 g. of cells per liter of the culture liquor.

EXAMPLE 3

Example 1 was repeated except that *Pichia aganobii* Y-145 was used in place of *Pichia aganobii* Y-16, and that the aerobic stirring culture was conducted at 28° C for 55 hours in place of 32° C for 53 hours. There was obtained 3.3 g. of cells per liter of the culture liquor.

EXAMPLE 4

Example 1 was repeated except that *Pichia aganobii* Y-1023 was used in place of *Pichia aganobii* Y-16. There was obtained 3.5 g. of cells per liter of the culture liquor.

EXAMPLE 5

Example 1 was repeated except that the culture liquor contains 2.5 g. of ethanol in place of 5 g. of methanol, that the preculturing was effected for 4 days in place of 48 hours, and that the aerobic stirring culture was conducted at 28° C. for 4 days in place of 32° C. for 53 hours. There was obtained 3.1 g. of cells per liter of the culture liquor.

EXAMPLES 6 – 8

Example 5 was repeated except *Pichia aganobii* Y-410, Y-145 and Y-1023 were used in place of *Pichia aganobii* Y-16, respectively. There were obtained 3.2 g., 3.3 g. and 3.2 g. of cells, respectively, per liter of the culture liquor.

What we claim is:

1. A process for producing yeast cells which comprises culturing aerobically a yeast belonging to *Pichia aganobii* in a culture liquor containing methanol and/or ethanol as a carbon source, nitrogen sources, inorganic salts and other nutrient sources, and recovering yeast cells therefrom.

2. A process according to claim 1 in which the yeast is *Pichia aganobii* Y-16, Y-145, Y-410 or Y-1023.

3. A process according to claim 1 in which the culture liquor contains up to 6 wt.% of methanol and/or ethanol, and the culturing is effected at 10° to 37° C. at a pH of 7.5 or less.

4. A process according to claim 1 in which the initial concentration of methanol and/or ethanol is controlled at 0.5 wt.% or less and the concentration of methanol and/or ethanol throughout the cultivation is maintained at a constant level by compensating as much methanol and/or ethanol as is consumed during cultivation.

5. A process according to claim 1 in which ammonia is added from time to time to the culture liquor, when ammonium salts are used as a nitrogen source.

6. A process according to claim 1 in which an assimilable carbohydrate is added to the culture liquor.

* * * * *